US006761684B1

United States Patent
Speier

(10) Patent No.: US 6,761,684 B1
(45) Date of Patent: Jul. 13, 2004

(54) ENDOSCOPE TIP PROTECTION SYSTEM

(75) Inventor: Craig J. Speier, Santa Barbara, CA (US)

(73) Assignee: Linvatec Corporation, Largo, FL (US)

( * ) Notice: Subject to any disclaimer, the term of this patent is extended or adjusted under 35 U.S.C. 154(b) by 104 days.

(21) Appl. No.: 09/636,198

(22) Filed: Aug. 10, 2000

(51) Int. Cl.[7] .................................................. A61B 1/00
(52) U.S. Cl. ........................ 600/121; 600/125; 600/175; 600/129
(58) Field of Search ................................. 600/121, 125, 600/129, 175, 176, 182, 114

(56) References Cited

U.S. PATENT DOCUMENTS

| 3,261,349 A | * | 7/1966 | Wallace | 362/574 |
| 4,254,762 A | * | 3/1981 | Yoon | 600/114 |
| 4,979,498 A | * | 12/1990 | Oneda et al. | 600/118 |
| 5,337,734 A | * | 8/1994 | Saab | 600/121 |
| 5,591,192 A | * | 1/1997 | Privitera et al. | 600/114 |
| 5,788,628 A | * | 8/1998 | Matsuno et al. | 600/121 |
| 5,817,015 A | * | 10/1998 | Adair | 600/121 |
| 5,863,287 A | * | 1/1999 | Segawa | 600/121 |
| 5,879,287 A | * | 3/1999 | Yoshihashi | 600/121 |
| 5,961,445 A | * | 10/1999 | Chikama | 600/112 |
| 6,019,719 A | * | 2/2000 | Schulz et al. | 600/109 |
| 6,095,811 A | * | 8/2000 | Stearns | 433/116 |
| 6,350,231 B1 | * | 2/2002 | Ailinger et al. | 600/121 |
| 6,387,044 B1 | * | 5/2002 | Tachibana et al. | 600/114 |

* cited by examiner

Primary Examiner—John P. Leubecker
(74) Attorney, Agent, or Firm—Gene Warzecha

(57) ABSTRACT

An endoscope tip protection system for shielding the optical component at the distal end of an endoscope. The system comprises a tubular sheath which is optically transparent at least at its distal end, and adapted to fit onto and be retained on the scope tip. The scope/sheath assembly is then inserted into an open ended tubular fiberoptic illuminating cannula which is adapted to receive the scope/sheath assembly and prevent the tubular sheath from falling out.

6 Claims, 3 Drawing Sheets

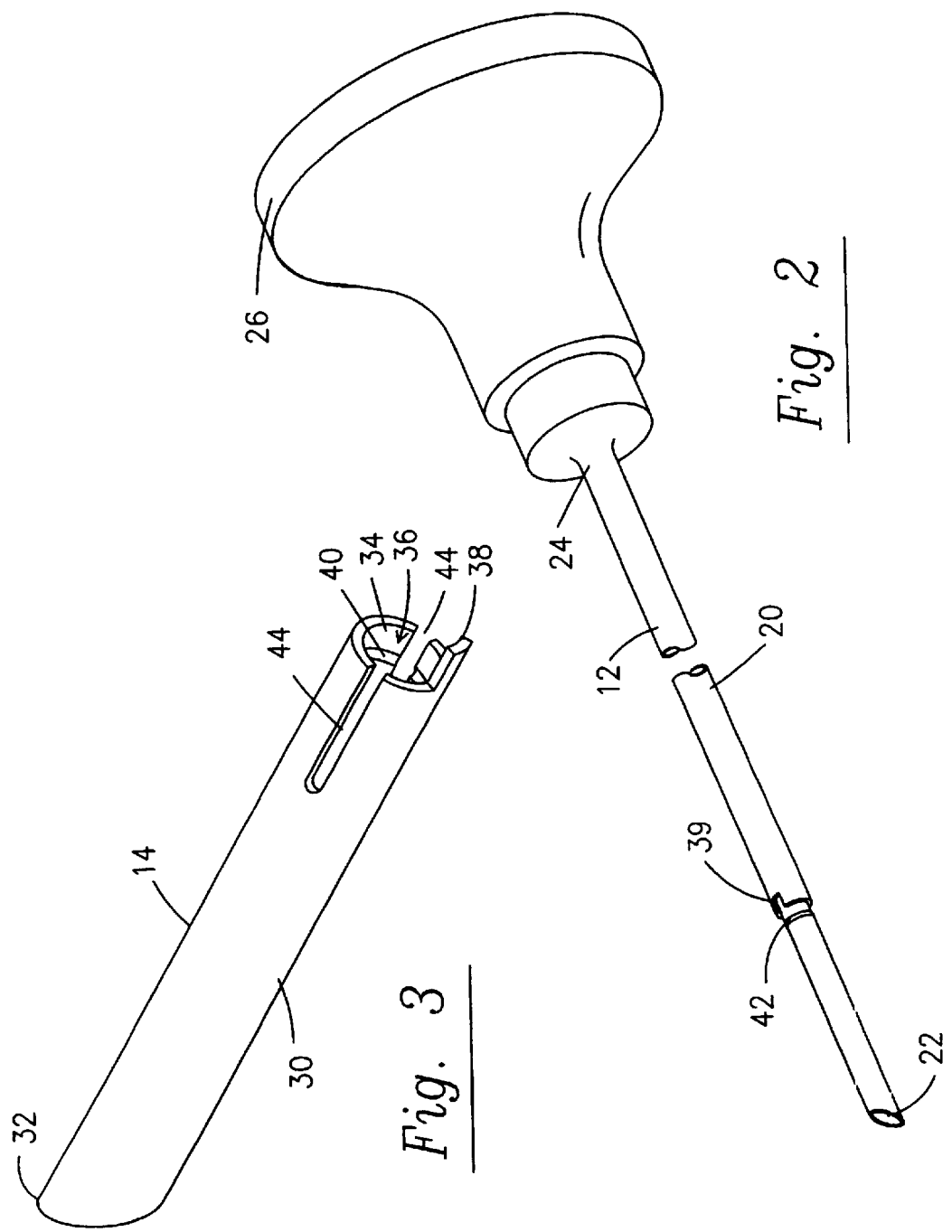

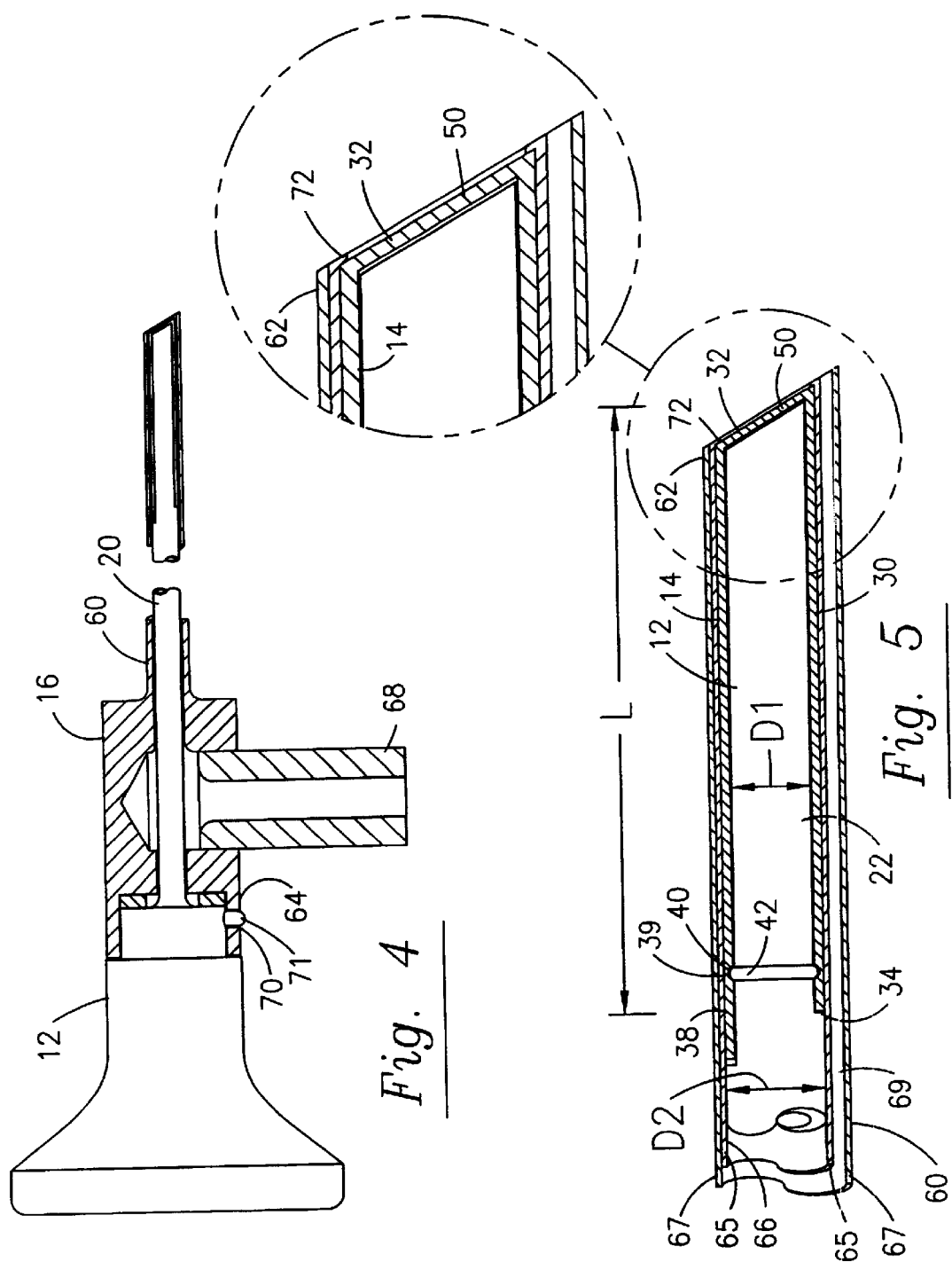

ENDOSCOPE TIP PROTECTION SYSTEM

BACKGROUND OF THE INVENTION

1. Field of the Invention

The invention relates to a system for protecting endoscopes during endoscopic surgical procedures. The invention is particularly suited to protect arthroscopes during arthroscopic surgery. Still more particularly, the invention relates to a disposable sheath adapted to shield the imaging optics at the distal tip of an arthroscope.

2. Description of the Prior Art

Arthroscopic surgical procedures require the use of elongated optical viewing devices (e.g. arthroscopes) and other instruments through one or more openings or portals of the body. Very often in diagnostic and operative arthroscopic surgical procedures an arthroscope is inserted in one portal while an instrument such as a manual or powered resecting instrument is inserted in another portal. The distal ends of the arthroscope and resecting instrument are manipulated by triangulation by the surgeon to resect or otherwise treat tissue at the surgical site.

The terms "endoscope" and "arthroscope" and the like may be used interchangeably herein. While the invention is described in terms of an arthroscope used for arthroscopic surgery, it is equally suited for endoscopic surgery in general where there is an interest in protecting the distal end of the endoscope. The terms "endoscope" and "endoscopic surgery" are used herein to refer to all minimally invasive surgical procedures and associated instruments used to access internal surgical sites through natural openings or other portals in a body (human or otherwise). Such procedures may include arthroscopy, laparoscopy, hysteroscopy, etc. While a scope used in these procedures may simply have an eyecup at the proximal end to enable direct observation by a surgeon, preferably the proximal end of the scope is adapted to interface with an image forming device such as a video camera to enable the procedure to be viewed on a monitor.

An arthroscope generally comprises an elongated rigid or flexible tubular shaft containing an optical (i.e. imaging) system aligned along the scope axis to transmit an image of the work site from its distal end to its proximal end. An objective lens or lens group is situated at the distal end of the scope to create an image and an ocular lens or lens group is situated at the proximal end to present the image to an observer through, for example, an interface with an image forming device such as a video camera. While the work site may be illuminated by a light source separate from the scope, preferably the arthroscope is sized to fit coaxially within a lumen of an illuminating sheath or cannula in the form of an elongated tube having open distal and proximal ends. An illuminating cannula contains fiberoptics or other illuminating light transmitting material to direct light from an input port at the proximal end of the illuminating cannula, through the wall of the cannula to its distal end. The arthroscope is concentrically assembled within the illuminating cannula so that the distal ends of both devices are in approximately the same plane and aligned either perpendicular to the concentric axes of the assembled scope and cannula or angled at some predetermined angle relative to the axes. The term "arthroscope" is sometimes used to refer to the scope portion of the device and sometimes used to refer to both the scope and cannula. In some cases, as for example in U.S. Pat. No. 5,377,669 (Shulz), the arthroscope and illuminating cannula are combined into a single endoscope.

During endoscopic surgery, the close proximity of the distal ends of the scope and the illuminating cannula to manual or powered resection instruments inserted through another portal frequently leads to inadvertent contact and resultant damage of either the optical system or fiberoptics by the resection instrument. Damage of the arthroscope may either destroy it or seriously degrade the image quality necessitating significant repair costs. Damage to the illuminating optics in the fiberoptic cannula is not as costly as damage to the imaging optical system although damage to either component results in less than optimal system performance and unwanted repair costs.

Protection of the distal end of an endoscope is available to some extent by prior art scopes which have interchangeable sheaths. As shown in U.S. Pat. No. 5,573,493 (Sauer et al.), for example, such prior art endoscopic sheaths contain the fiberoptics as well as a prism to change the angle of view. Similar fiberoptic and lens containing (interchangeable) endoscope tips are shown in U.S. Pat. Nos. 4,747,661 (Ohkuwa) and 4,765,313 (Kumakura). While these tips are smaller than the aforementioned interchangeable sheath, they are still relatively costly. While intended to be replaceable, these sheaths and tips contain costly elements and do not efficiently protect the endoscope tip.

Prior art interchangeable sheaths that include fiberoptics result in decreased fiberoptic transmission due to the inefficiency of transmission at the tip interface. Additionally sheaths that cover both the distal tip of the illuminating light path and the imaging optics produce internal reflections (of illuminating light) from the distal face of the sheath, which reflections may stray into the imaging optics and degrade the image.

Prior art sheaths that have optical portions are costly if made from the type of glass which is necessary to achieve high optical performance and efficiency. Therefore, it is difficult, if not simply impractical to make such sheaths disposable. If they were made inexpensively in order to be disposable, they would suffer poor optical performance. Additionally, alignment of the sheath objective portion is difficult to achieve and, consequently, interchangeable tips must be made to tight tolerances that must be maintained to prevent image degradation due to misalignment. This also contributes to increased cost.

It is, therefore, an object of the present invention to produce an endoscope system which protects the optical system of an endoscope, in particular its distal end.

It is a further object of this invention to provide a protection system for protecting the distal tip of an endoscope from inadvertent damage during surgical procedures.

It is an additional object of this invention to provide a protection system for protecting the distal tip of an endoscope from inadvertent damage without compromising the image quality.

It is also an object of this invention to provide an endoscope which may be easily repaired if damaged.

It is yet another object of this invention to produce an endoscope tip protection system adaptable to a variety of endoscope viewing angles.

It is still another object of this invention to produce an endoscope tip protection system which is disposable.

SUMMARY OF THE INVENTION

These and other objects of this invention are embodied in an endoscope tip protection system comprising a tubular sheath having an open proximal end, a closed, optically transparent distal end and an internal bore therebetween. The endoscope has a proximal, viewing end and a distal objective end adapted to be received and selectively attached within the internal bore of the sheath. The assembled distal ends of the endoscope and the tubular sheath are adapted to be selectively received within a fiberoptic illumination cannula having an internal bore, an open proximal end and an open distal end.

BRIEF DESCRIPTION OF THE DRAWINGS

FIG. 2 is a front perspective view of the arthroscope portion of the system shown in FIG. 1.

FIG. 3 is a rear perspective view of the protective tip sheath of the invention shown in FIG. 1.

FIG. 4 is a cross-sectional view of the components of FIG. 1 shown assembled.

FIG. 5 is an enlarged portion of the distal end of the assembly shown in FIG. 4.

DESCRIPTION OF THE PREFERRED EMBODIMENT

Figure 1:
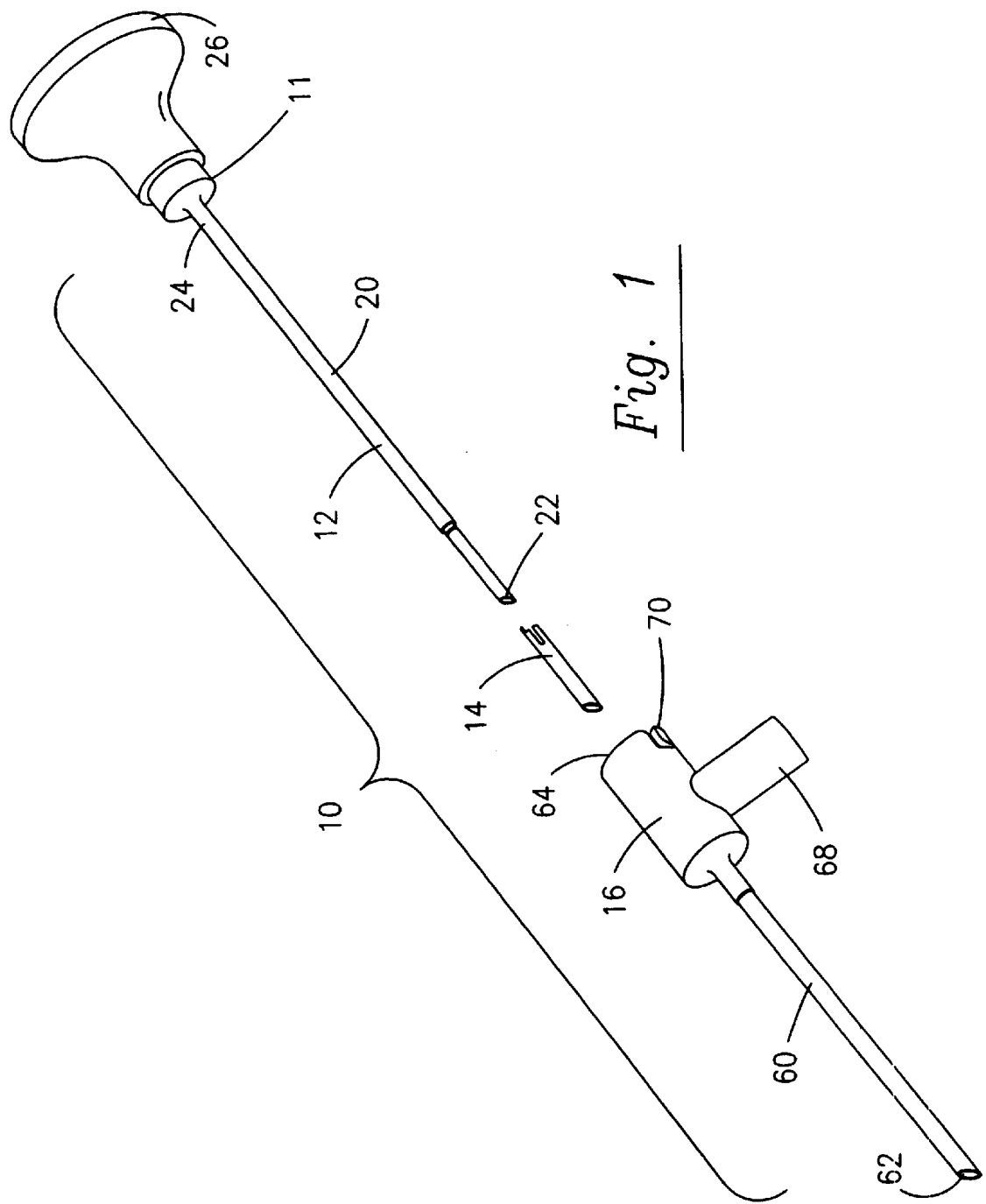
FIG. 1 shows an exploded front perspective view of a preferred embodiment of an endoscope tip protection system constructed in accordance with the principles of this invention.

Referring now to the drawings, there is shown an arthroscope 10 constructed in accordance with the principles of this invention. Arthroscope 10 comprises a scope portion 12, a protective sheath 14 adapted to be received on the scope portion and an illuminating cannula 16 adapted to receive the assembled scope and protective sheath.

Scope 12 is an elongated instrument having shaft 20, a distal, objective end 22 and a proximal, viewing end 24. Proximal end 24 is provided with an image-forming device 26. Image forming device 26 is shown in the form of an eyepiece although it will be understood that it could also be a coupler adapted to be selectively or permanently engaged to a video camera (not shown). Any suitable image-forming device may be used. Shaft 20 contains along its axis an elongated optical image transfer system (not shown) to transfer an image from distal end 22 to image forming device 26. In the preferred embodiment, shaft 20 contains a rod lens system to transfer the image to a proximally situated optical coupler. However, the invention is equally suitable for protection of the distal optical system used with prior art arthroscopes which utilize a distally situated semi-conductor image forming device. While in prior art devices, the arthroscope shaft 20 is cylindrical and has a uniform diameter along its length, the shaft 20 of scope 12 has a proximal end 22 having a diameter D1 over a predetermined distally situated length L, diameter D1 being less than that of diameter D2 of the remainder of shaft 20 (best seen in FIG. 5).

Protective sheath 14 comprises a cylindrical body 30 having a closed distal end 32 and an open proximal end 34. Sheath 14 has an internal bore 36 with an inside diameter D1 equal to the outside diameter of the distal tip of scope 12. The term "equal" will be understood to mean that the diameters of the bore and scope are provided with some clearance to enable the components to fit together. The thickness of the cylindrical wall 30 is such that the outer diameter of body 30 is substantially equal to diameter D2 of the scope shaft.

In the preferred embodiment, the proximal end of protective sheath 14 is provided with a key 38 adapted to mate with a corresponding recess 39 on scope 12 in order to properly orient the sheath relative to the scope. While such an orienting mechanism is helpful if the distal tips of the scope and sheath are angled as shown in FIG. 5, such orientation may not be necessary if the distal tips of the scope and sheath are perpendicular to their axes. The proximal end of sheath 14 is provided with some mechanism to selectively attach it to the distal end of scope 12. Such retention may be effected by a friction fit facilitated by appropriately sizing the various components or by a variety of other means. In the preferred embodiment, sheath 14 is provided with an annular groove 40 designed to mate with a complementarily shaped rib 42 on the outer surface of scope 12. The proximal end of sheath 14 has two diametrically opposed slits 44 to enable the rib and groove arrangement to engage.

The distally facing transverse end wall 50 of sheath 14 must be as optically transparent as possible in order to not introduce any aberrations into the image created by scope 12. However, the cylindrical wall, body 30 may either be formed from the same material as end wall 50, with obviously less attention to optical transparency, or may be formed of any other suitable material (metal, plastic, etc.).

While ideally made inexpensively enough to be disposable, the protective sheath may be made reusable so that the protective sheath need not be discarded if no damage has occurred.

Illuminating cannula 16 comprises a tubular body 60 having an open distal tip 62 and an open proximal end 64 with an internal bore 66 adapted to receive the scope/protective sheath assembly. Cannula 16 is formed of an inner tube 65 and an outer tube 67 which define an annular space therebetween. In the preferred embodiment the annular space contains a plurality of fiberoptic fibers extending from light port 68 to distal tip 62. The fibers 69 may be uniformly distributed circumferentially throughout the annular space or, as shown in FIG. 5, may be asymmetrically distributed such that the axis of cannula 16 will be parallel to and not coincident with the axis of scope 12 when the scope and cannula are assembled (i.e. the annular space is eccentrically situated relative to the axis of the outer tube). Cannula 16 is attached to scope 12 by a J-slot 70 and pin 71 combination in a conventional manner.

As best seen in FIG. 5, the distal end 62 of illuminating cannula 16 has a radially inwardly extending annular flange 72 or other suitable projection to prevent protective sheath 14 from falling out of the illuminating cannula and into the patient. The size of flange 72 must be minimized in order to avoid blocking the field of view of scope 12.

It will be understood that numerous modifications may be made to the preferred embodiment of the invention disclosed herein without departing from the spirit and scope thereof.

What is claimed is:

1. An endoscope tip protection system comprising:
   an optically transparent, hollow and disposable tubular sheath comprising an outer surface, an open proximal end, a closed, optically transparent distal end and a hollow internal bore extending therebetween, said bore adapted to receive a distal portion of an endoscope;
   an endoscope comprising a proximal, viewing end and a distal end, said distal end comprising an objective lens system and adapted to be received within said internal bore;
   attachment means for selectively and non-hermetically attaching and detaching said distal end of said endoscope within said internal bore of said tubular sheath, said tubular sheath outer surface having a cross-section which is substantially the same as the cross-section of the outer surface of said endoscope at a point proximal to said tubular sheath, said attachment means effected by cooperative action between said tubular sheath and said endoscope at a point intermediate said distal and proximal ends of said endoscope; and a fiberoptic illumination cannula having an internal bore, an open proximal end and an open distal end, said illumination cannula adapted to selectively receive therein said distal end of said endoscope and said tubular sheath.

2. An endoscope tip protection system according to claim 1 wherein said attachment means comprises an annular rib on said tubular sheath and a complementarily shaped mating annular groove on said endoscope.

3. An endoscope tip protection system comprising:

an optically transparent, hollow and disposable tubular sheath comprising an open proximal end, a closed, optically transparent distal end and a hollow internal bore extending therebetween, said bore adapted to receive a distal portion of an endoscope;

an endoscope comprising a proximal, viewing end and a distal end, said distal end comprising an objective lens system and adapted to be received within said internal bore;

attachment means for selectively attaching said distal end of said endoscope within said internal bore of said tubular sheath; and a fiberoptic illumination cannula having an internal bore, an open proximal end and an open distal end, said illumination cannula adapted to selectively receive therein said distal end of said endoscope and said tubular sheath wherein said open distal end of said illumination cannula comprises a radially inwardly directed projection means for preventing longitudinally outward movement of said tubular sheath.

4. An endoscope tip protection system according to claim 3 wherein said projection means comprises an annular, inwardly directed flange adapted to abut said distal end of said tubular sheath.

5. A surgical endoscope comprising:

an elongated optical viewing member having a distal end for viewing a work site, a proximal end for presenting an image to an observer and an intermediate section for transmitting an image from said distal end to said proximal end;

an elongated illuminating light transmission cannula having a proximal end adapted to receive said elongated optical viewing member therethrough and to receive illuminating light from a light source, a distal end for illuminating said work site, and an intermediate section for transmitting said illuminating light from said proximal end to said distal end, wherein said distal end of said illuminating light transmission cannula comprises an inwardly extending projection for preventing motion of said protective tip means from said sheath;

a selectively attachable optically transparent, hollow protective tip means having an open proximal end and a closed distal end, said tip means interposed between said distal end of said optical viewing member and said illuminating cannula, said tip means having a hollow internal bore extending between its proximal and distal ends for being received on said distal end of said optical viewing member; and means for releasably attaching said protective tip means over said distal end of said elongated optical viewing member.

6. A surgical endoscope according to claim 5 wherein said distal end of said illuminating light transmission cannula comprises an inwardly extending annular flange.

* * * * *